United States Patent [19]

Sajtos

[11] Patent Number: 4,769,464
[45] Date of Patent: Sep. 6, 1988

[54] PROCESS FOR THE PREPARATION OF MONOCARBONYL OR BISCARBONYL COMPOUNDS

[75] Inventor: Alexander Sajtos, Linz, Austria

[73] Assignee: Chemie Linz Gesellschaft m.b.H., Linz, Austria

[21] Appl. No.: 681,904

[22] Filed: Dec. 17, 1984

[30] Foreign Application Priority Data

Dec. 23, 1983 [AT] Austria ................................ 4500/83

[51] Int. Cl.$^4$ ...................... C07B 41/06; C07C 45/40; C07D 213/48; C07D 213/50
[52] U.S. Cl. ................................... 546/314; 546/315; 568/309; 568/311; 568/320; 568/385; 568/401; 568/430; 568/469
[58] Field of Search ............... 546/314, 315; 568/309, 568/385, 311, 320, 401, 430, 469

[56] References Cited

U.S. PATENT DOCUMENTS

| 3,145,232 | 8/1964 | Thompson | 568/338 |
| 3,637,721 | 1/1972 | Pappas et al. | 546/340 |
| 3,705,922 | 12/1972 | Callighan et al. | 562/587 |

FOREIGN PATENT DOCUMENTS 709450 5/1954 United Kingdom .
590314 1/1978 U.S.S.R. .

OTHER PUBLICATIONS

Rylander, P. N. "Catalytic Hydrogenation over Platinum Metals" Academic Press (1967) pp. 18–19; pp. 16–17.

Primary Examiner—Mary C. Lee
Assistant Examiner—Dale A. Bjorkman
Attorney, Agent, or Firm—Mark Dryer

[57] ABSTRACT

The invention relates to a process for the preparation of monocarbonyl or biscarbonyl compounds by reacting organic carbon compounds having one or more olefinic or aromatic double bonds in the molecule with the equivalent amount of ozone and by subsequently catalytically hydrogenating the ozonization products, wherein the peroxide-containing ozonization solution is fed continuously into a suspension of the hydrogenation catalyst in a lower aliphatic alcohol, while a peroxide content of not more than 0.1 mole/l is maintained, and the ozonization products are continuously cleaved reductively to give the corresponding carbonyl compounds.

14 Claims, No Drawings

PROCESS FOR THE PREPARATION OF MONOCARBONYL OR BISCARBONYL COMPOUNDS

The invention relates to a process for the preparation of monocarbonyl or biscarbonyl compounds from unsaturated organic carbon compounds containing one or more olefinic or aromatic double bonds in the molecule.

The preparation of carbonyl compounds from organic compounds containing, as a structural element, one or more C=C double bonds in the molecule by means of a two-stage ozonolysis and reduction process is known. In carrying out this method, an excess of ozone is in most cases used in the first stage in order to achieve as complete an ozonization as possible of the double bond. The reductive cleavage which follows in the second stage constantly causes difficulties, since the peroxide-containing ozonization products are unstable and, in the presence of metallic hydrogenation catalysts, undergo rearrangement reactions particularly readily before they can be reduced to give the corresponding carbonyl compounds. In addition, losses in the activity of a catalyst are observed when noble metal catalysts are in prolonged contact with peroxide-containing solutions, so that the solutions do not as a rule become entirely peroxide-free through hydrogenation in the reductive cleavage, and, in addition to difficulties in preparing the end products in a pure state, it is necessary to accept losses in the yield.

In order to avoid these difficulties, a process for the preparation of carbonyl compounds is recommended in U.S. Pat. No. 3,145,232, in which the reductive cleavage after the ozonolysis is carried out at temperatures below $-40°$ C. in the presence of a trialkyl phosphite. Besides the outlay on apparatus for the production of the extremely low reaction temperatures, such a method of carrying out the reaction requires the use of absolutely anhydrous solvents, since the trialkyl phosphites are hydrolysed extremely rapidly in solvents containing water. In addition, the removal of the free carbonyl compunds from the phosphate esters formed in the reduction causes considerable difficulties.

Since it has been shown that low reaction temperatures have a disadvantageous effect on the activity of the reducing agents employed, and losses in yield arise on this account, in a process for the preparation of aliphatic, aromatic and hetero-aromatic aldehydes, such as is described in U.S. Pat. No. 3,637,721, although the ozonolysis of the C=C double bond is carried out at $-50°$ C., the reaction temperatures during the course of the reductive cleavage of the ozonization products by means of aromatic or aliphatic disulfides are raised to 50° C. However, in the said process, the separation of the sulfoxides formed as accompanying products in the reduction, for example dimethyl sulfoxide, from the aldehydes formed as process products turns out to be extremely difficult and in many cases cannot be effected at all without forming derivatives of the aldehydes.

Finally, U.S. Pat. No. 3,705,922 or German Offenlegungsschrift No. 2,514,001 describe the preparation of carbonyl compounds by means of an ozonolysis and reduction process in which the unsaturated compounds serving as the starting material are reacted with an excess of ozone and the ozonization products thus formed are cleaved reductively by catalytic hydrogenation. In this process, however, it is necessary to remove excess ozone again, in a separate process, by flushing the reaction solution with an inert gas, for example with nitrogen, before the reductive cleavage, in order to protect the hydrogenation catalyst against losses in activity.

The hydrogenation is carried out by then adding the catalyst, which is preferably a noble metal catalyst, directly to the reaction mixture formed in the ozonolysis, and passing in hydrogen until saturation is reached. Since noble metal catalysts become deactivated when in prolonged contact with organic peroxides, in the case of the known processes the yield in the hydrogenation depends on the amount of hydrogenation catalyst employed in a particular case. As can be seen from a comparison of the examples in U.S. Pat. No. 3,705,922, in spite of a correspondingly prolonged reaction time, the yield decreases by about 10%, if, for the same batch size, only 0.2 g of a Pd/Al$_2$O$_3$ catalyst is used instead of 0.5 g. Nor is information to be found in the publications mentioned regarding the possibility of regenerating or re-using the noble metal catalyst employed, after the completion of the hydrogenation.

It has now been found, surprisingly, that the disadvantages attaching to the known processes can be avoided, in accordance with the present invention, by means of a simple and economical process in which an unsaturated organic carbon compound containing one or more olefinic or aromatic double bonds is reacted with one molar equivalent of ozone, avoiding any excess, and the peroxide-containing ozonization products are then rapidly cleaved reductively by catalytic hydrogenation in a dilute solution at a low concentration of peroxides.

In comparison with the known processes, the process according to the invention provides carbonyl compounds in a better yield and purity and by a simpler and more economical route. The catalysts are protected in the process according to the invention and are not poisoned to an evident extent over a prolonged operating life, so that they exhibit no noticeable loss in activity when re-used, even without regeneration and working up. In view of the state of the art, all these advantageous properties are surprising.

The present invention accordingly relates to a process for preparing monocarbonyl or biscarbonyl compounds of the formula

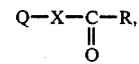   I wherein
Q represents hydrogen or the radicals

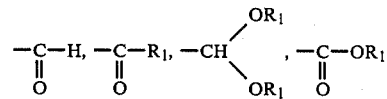

in which R$_1$ is C$_1$ to C$_6$ alkyl,
X represents linear or branched alkylene having 1 to 20 C atoms, linear or branched alkylene having 2 to 20 C atoms in which one —CH$_2$-group of the alkylene chain is replaced by oxygen or the —SO$_2$-group, substituted linear or branched alkylene having 1 to 20 C atoms, this alkylene being substituted by one or more groups which are inert under the reaction conditions; aralkylene or alkylenearylene having 7–12 C atoms each; substituted aralkylene or alkylenearylene having 7–12 C atoms each, the substituent being a group which is inert under the reaction conditions; o-, m-, or p-phenylene; substituted o-, m- or p-phenylene, the substituent being a group which is inert under the reaction conditions; a divalent five-membered or six-membered heterocyclic radical, containing one or two heteroatoms in the heterocyclic ring; or a single bond between two adjacent C-atoms; and R represents hydrogen, $C_1$ to $C_4$ alkyl or the group

wherein $R_1$ is defined as above; glyoxal, alkylglyoxales and dialkylacetals thereof being disclaimed from the formula I, said process consisting of (a) reacting an unsaturated compound of the formula

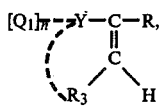   II wherein n is 0 or 1, $Q_1$ represents hydrogen or the radicals

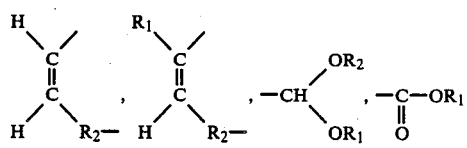

in which $R_1$ is $C_1$ to $C_6$ alkyl;

$R_2$ and $R_3$ independently of one another represent hydrogen, $C_1$ to $C_4$ alkyl or, if n is 1 and $Q_1$ represents the radical

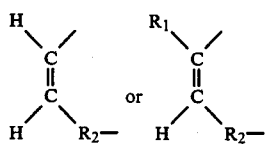

$R_2$ and $R_3$ together can be a further single bond between two adjacent C atoms or alkylene having 2 to 4 carbon atoms; Y has the same meaning as X in formula I if n is 1, or, if n is o, Y together with $R_3$ represents linear or branched alkylene having 2 to 20 C atoms, linear or branched alkylene having 2 to 20 C atoms in which one —$CH_2$-group of the alkylene chain is replaced by oxygen or the —$SO_2$-group, substituted linear or branched alkylene having 2 to 20 C atoms, this alkylene being substituted by one or more groups which are inert under the reaction conditions, aralkylene or alkylenearylene having 7–12 C atoms, substituted aralkylene or alkylenearylene having 7–12 C atoms, the substituent being a group which is inert under the reaction conditions; and R is defined as in formula I, is reacted in a lower aliphatic alcohol, at temperatures from −80° C. to +20° C. with the equivalent amount of ozone to yield a peroxide-containing solution of the ozonisation products of the compound of formula II (b) hydrogenating the peroxide-containing solution of the ozonisation products thus obtained at pH 2 to 7 and at temperatures from 15° to 45° C., said solution being fed continuously, while hydrogen is passed in under a pressure of 1 to 20 bar, into a suspension of a noble metal catalyst in the lower aliphatic alcohol used in stage (a), at such a rate that, over the entire course of hydrogenation, a peroxide content of not more than 0.1 mole/l is set up and maintained in the suspension, whereby the ozonisation products are cleaved reductively into the corresponding carbonyl compound, and then separating the carbonyl compound so formed.

In the event that (a) methyl methacrylate or (b) sulfolene is used as the starting material, the process according to the invention can be described by the formulae below:

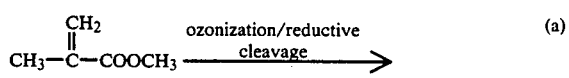   (a)

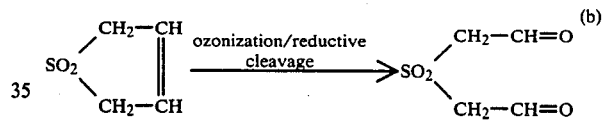   (b)

Especially suitable starting materials which can be reacted to give the corresponding monocarbonyl or biscarbonyl compounds of the formula I are compounds of the formula II in which Y or Y together with $R_3$ represents alkylene having 2 to 10 carbon atoms, aralkylene or alkylenearylene having 7–10 carbon atoms. The above mentioned radicals can also be substituted by one or more groups which are inert under the reaction conditions, for example alkyl, alkoxy or alkoxy carbonyl groups having in each case 1 to 4 carbon atoms, or by nitro groups.

In a preferred manner unsaturated compounds of the formula

   IIa in which $Y_1$ together with hydrogen represents a phenyl radical which is substituted in the ortho-, meta- or para-position or a six-membered hetero-aryl radical having one hetero-atom in the ring, but particularly preferably represents the para-nitrophenyl-, p-tolyl, 2-pyridinyl or 4-pyridinyl radical, are reacted to give the correspondingly preferred carbonyl compounds. Examples of unsaturated compounds of the formula IIa are para-nitrostyrene or para-methylstyrene and also 2-vinylpyridine or 4-vinylpyridine.

It is also preferable to react unsaturated compounds of the formula

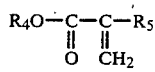  IIb in which R$_4$ denotes methyl or ethyl and R$_5$ denotes methyl, ethyl or the ethoxycarbonyl radical, to give the correspondingly preferred carbonyl compounds. Compounds which are reacted very particularly preferentially are those in which R$_4$ and R$_5$ denote methyl. Examples of starting compounds of the formula II b are methyl methacrylate, an ethyl alklyacrylate or diethyl methylenemalonate.

A further preferred group of starting materials for the preparation of the correspondingly preferred carbonyl compounds of the formula I is formed by compounds of the formula

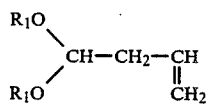  IIc in which
R$_1$ is as defined in formula I. Examples of compounds of the formula IIc are 4,4-dimethoxybutene or 4,4-di-n-butoxybutene.

Compounds of the formula

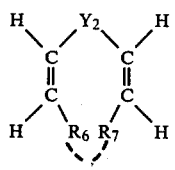  IId in which
Y$_2$ denotes an o-phenylene radical or an alkylene radical having 2 to 4 C atoms and R$_6$ and R$_7$ together denote a single bond between the adjacent C atoms or an alkylene radical having 2 to 4 C atoms, are also reacted in a preferred manner to give the correspondingly preferred dialdehydes of the formula I. Examples of compounds of the formula IId are naphthalene or 1,5-cyclooctadiene.

Finally, a further group of unsaturated compounds of the formula

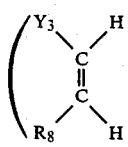  IIe in which
Y$_3$ and R$_8$ together denote an alkylene radical having 2 to 6 C atoms or the radicals

—CH$_2$—SO$_2$—CH$_2$—, —CH$_2$—O—CH$_2$—,

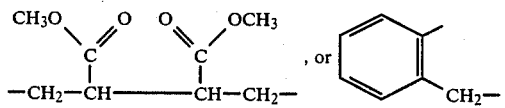

are reacted in a preferred manner to give the correspondingly preferred dialdehydes of the formula I.

Examples of compounds of the formula IIe are cyclohexene, cyclooctene, sulfolene, indene, dimethyl tetrahydrophthalate or 2,5-dihydrofuran.

The ozonization is preferably carried out at temperatures from −30° to 0° C.; on the other hand, it is particularly preferable to maintain a temperature from −15° to 0° C.

In the process according to the invention, the particular unsaturated compound of the formula II which is reacted is treated with precisely the equivalent amount of ozone, there being a quantitative conversion of ozone and stoichiometric amounts of the starting materials of the formula II being consumed under the process conditions described. As a result of avoiding an excess of ozone it is possible to prevent the tendency, observed in some cases during the ozonization of olefinic double bonds, for the reaction mixture to decompose spontaneously in an explosive manner, nor is it necessary any longer to ensure that, after the completion of the ozonization, excess or unreacted ozone is expelled from the reaction mixture before hydrogenation.

The reaction of the unsaturated compounds with ozone in stage (a) is carried out in a lower aliphatic alcohol in which the starting compounds are readily soluble. Preferred solvents are, above all, methanol or ethanol, but, on the other hand, the use of methanol is particularly preferred.

In the process according to the invention, the catalytic hydrogenation of the ozonolysis products which follows the ozonization is carried out in a highly dilute solution, care being taken by means of suitable measures and devices, that a peroxide content of not more than 0.1 mole/l, preferably not more than 0.05 mole/l and especially not more than 0.02 mole/l is set up and maintained in the hydrogenation solution during the entire hydrogenation.

In order to carry out the process in practice, a suspension of the catalyst in the alcohol used in the ozonization in stage (a), preferably methanol or ethanol, very particularly methanol, is initially placed in, for example, a hydrogenation reactor, and the solution obtained in the ozonization is fed in continuously by means of a controllable metering device. In adding the ozonolysis solution at the start of, and in the course of, the hydrogenation, care must, of course, be taken that the abovementioned peroxide content in the hydrogenation solution is not exceeded as a result of the amount of peroxide-containing ozonization products added.

As a result of the low concentration of peroxide-containing ozonization products during the actual hydrogenation process, the ratio of catalyst to the substrate to be reduced is uniformly advantageous throughout the entire duration of the hydrogenation, so that rapid reduction is ensured even if the catalyst is employed sparingly. The poisoning which can otherwise be observed at high peroxide concentrations and the associated loss in activity of the catalyst are also prevented in this manner.

Viewed as a whole, however, a large amount of ozonization products can be cleaved reductively in a relatively small volume because these products are fed in continuously, as a rseult of which concentrated solutions are obtained in the final stage of the process and savings are made, not solely in the solvent itself but also in time and expense when the solvents are removed by distillation during working up.

Suitable catalysts are the noble metal catalysts customarily used for hydrogenation reactions, and these can be employed in the form of powder catalysts together with supporting materials or without a supporting material. It is preferable to use palladium or platinum catalysts, in particular platinum catalysts without a supporting material. In the case of powder catalysts, examples of suitable supporting materials are charcoal, aluminum, silicia gel or kieselguhr. The yields in the process according to the invention are in themselves independent of the amount of catalyst employed, but, in order to achieve an adequate hydrogenation rate, it is advisable initially to take the catalysts mentioned in amounts, of noble metal, of 0.1 to 5% by weight, preferably 0.5 to 2% by weight, relative to the particular total amount of ozonization products fed in per hour.

The hydrogenation is continued until no further absorption of hydrogen can be detected. In the process according to the invention equivalent amounts of hydrogen are consumed for the reduction of the ozonization products. The amount of hydrogen which can be used in the hydrogenation extends from 1 molar equivalent up to a several times molar excess. The use of excess hydrogen affords no advantages in itself and is only expedient in order to ensure an adequate supply of hydrogen to the hydrogenation mixture.

In the process according to the invention, the hydrogenation is advantageously carried out under conditions of virtually atmospheric pressure.

Conditions of virtually atmospheric pressure are to be understood here as meaning pressures from 1 to about 3 bar, such as are customary in the art in order to prevent the penetration of air into the hydrogenation reactor. The reduction of the ozonization products can be carried out very easily in this way from the point of view of technical considerations and apparatus. However, it is also possible to carry out the hydrogenation at a pressure of up to 20 bar and thus to increase the rate of hydrogenation.

The reductive cleavage takes place exothermically and, in accordance with a preferred embodiment of the present invention, is carried out at 20° to 40° C., preferably at temperatures within the range from 35° to 40° C.

It is advantageous to maintain a pH value of 3 to 5 during the hydrogenation. Since acid by-products are formed in small amounts during the course of the hydrogenation, the metered addition of a base, advantageously dilute sodium hydroxide solution, is necessary in order to maintain the desired pH value.

Under the conditions of the process according to the invention, an alcoholic solution of the process products which is entirely free from peroxides and can be worked up in a non-dangerous manner is obtained when the hydrogenation is complete. Before the reaction mixture is worked up, the catalyst is removed by one of the known methods, for example by filtration, decantation or centrifuging, and the solvent is recovered, preferably by being distilled off.

The catalyst which has been removed from the reaction mixture is used for reductive cleavage in further reaction cycles, without regeneration or working up, no loss in the activity of the catalyst being observed. It is expedient to follow a procedure in which, after the completion of the hydrogenation, the contents of the hydrogenation reactor are removed by suction until a residual amount of the hydrogenation solution, amounting, for example, to one-fifth to one-tenth of the original capacity of the reactor, remains in the reactor, together with the catalyst. A new batch of ozonization products can then be metered into this residue under the conditions mentioned above and can be cleaved reductively by passing in hydrogen. Surprisingly, the reductive cleavage can be carried out, under the conditions of the process according to the invention, using the same catalyst in a large number of successive reaction cycles, for example 10 to 100, at about the same yield and about the same consumption of hydrogen as in the first reaction cycle.

In some cases it can be advantageous to remove the cations present in the reaction mixture as a result of the addition of a base, for example by treating the solution with an acid ion exchanger, before the solvent is removed.

The process products can be worked up and prepared in a pure form by the customary chemical methods, for example by rectification, extraction or crystallization.

The unsaturated carbon compounds of the formula II required at starting substances are either commercially available substances or are accessible in a simple manner by known chemical methods. Thus, for example, the 2-vinylpyridines or 4-vinylpyridines of the formula IIa are readily obtainable by reacting picolines with formaldehyde. Alkyl alkylacrylates of the formula IIb, in particular methyl methacrylate as a starting material for the preparation, according to the invention, of methyl pyruvate, are products which can be prepared on a large industrial scale. Dialkoxybutenes of the formula IIc can be obtained in an economical manner and in very good yields, for example by dimerizing alkyl vinyl ethers using catalytic amounts of $HgF_2$. The starting compounds of the formulae IId and IIe, for example cyclooctadiene, naphthalene, cyclooctene, cyclohexene, sulfolene, indene, dimethyl tetrahydrophthalate or 2,5-dihydrofuran, are readily accessible, commercially available substances.

The process products of the formula I are valuable starting materials and intermediate products from which a large number of chemical compounds of different structures or substances having, for example, a high biological and pharmacological importance can be prepared.

The process according to the invention is illustrated in greater detail in the following examples.

EXAMPLE 1 p-tolualdehyde 17.7 g of p-methylstyrene, dissolved in 1 l of methanol, are reacted with the equivalent amount of ozone at −10° C. by passing in an $O_2/O_3$ mixture containing 4% by weight of ozone. In this reaction, ozone is absorbed quantitatively and the residual content of p-methylstyrene after the completion of the ozonization is less than 1% of the starting concentration.

The solution obtained in the ozonization is fed continuously, via a metering vessel, into a hydrogenation reactor in which a suspension in 200 ml of methanol of 1 g of platinum, prepared in situ by hydrogenating $PtO_2$, has been placed beforehand and which is filled with hydrogen, at such a metered rate that the peroxide content in the hydrogenation solution does not exceed 0.02 mole/l at the start and in the course of the whole hydrogenation. Hydrogenation is carried out with vigorous stirring and the addition of hydrogen until a sample gives a negative peroxide test, the temperature being kept at 30° to 40° C. by external cooling. The hydrogen consumed is replenished continuously from a stock vessel, and a pH value of 4 to 5 is maintained in the solution by adding methanolic NaOH. When the addition of the ozonization solution is complete, the absorption of hydrogen ceases within a few minutes and the reaction solution is completely free from peroxides. A total of 31.4 standard liters of hydrogen, corresponding to 93.4% of theory, are absorbed during the hydrogenation.

The mixture is worked up by filtering off the catalyst and rendering the reaction solution free from sodium by stirring with a strongly acid ion exchanger (Lewatit). After the catalyst has been removed, the solvent and volatile accompanying products are removed on a rotary evaporator and the residue containing the reaction product is rectified in vacuo.

This gives 169 g of p-tolualdehyde boiling at 106°–108° C./10, corresponding to a yield of 94% of theory.

EXAMPLE 2 p-nitrobenzaldehyde 224 g of p-nitrostyrene are dissolved in 1 liter of methanol and reacted with ozone and subsequently hydrogenated analogously to the procedure indicated in Example 1. The absorption of hydrogen is 31.4 standard liters, corresponding to 93.4% of theory.

The mixture is worked up by removing the methanol, together with the volatile accompanying products, on a rotary evaporator, dissolving the residue in hot water and then cooling the solution in an ice bath. 216 g of pure p-nitrobenzaldehyde of melting point 105°–106° C. then crystallized out, corresponding to a yield of 95.5% of theory.

EXAMPLE 3 pyridine-4-aldehyde 158 g of 4-vinylpyridine are dissolved in 1 liter of methanol and reacted with ozone and subsequently hydrogenated analogously to the procedure indicated in Example 1. 29.8 standard liters of hydrogen are absorbed during the hydrogenation, corresponding to 88.7% of theory.

Working up is carried out as in Example 1, and the residue containing the reaction product is fractionated in vacuo. This gives 147 g of pyridine-4-aldehyde boiling at 70° to 72° C./10, corresponding to a yield of 91.5% of theory.

EXAMPLE 4 pyridine-2-aldehyde 158 g of 2-vinylpyridine are dissolved in 1 liter of methanol and reacted with ozone, and subsequently hydrogenated, analogously to the procedure indicated in Example 1. 28.9 standard liters of hydrogen, corresponding to 86% of theory, are absorbed during the hydrogenation.

Working up is carried out as in Example 1, and the residue containing the reaction product is purified by rectification. 143 g of pyridine-2-aldehyde boiling at 59°–62° C. 10, corresponding to a yield of 89.1% of theory, are obtained thereby.

EXAMPLE 5 methyl pyruvate 150 g (1.5 moles) of methyl methacrylate are dissolved in 1 l of methanol and reacted with the equivalent amount of ozone at $-10°$ to $-5°$ C. by passing in an air/$O_3$ mixture. After the completion of the ozonization, the residual content of methyl methacrylate in the reaction mixture is less than 1% of the initial concentration.

A suspension of 1 g of platinum in 200 ml of methanol is initially placed in a hydrogenation reactor, and the ozonization solution is added dropwise continuously, with vigorous stirring during the hydrogenation, at such a rate that the peroxide concentration in the hydrogenation solution does not exceed a concentration of 0.1 mole/l. The hydrogenation is carried out at a temperature of 30° to 40° C. and at a pH of 4 to 5, which is adjusted by means of an automatic titration with methanolic sodium hydroxide solution, and the hydrogenation is continued, with replenishment of the hydrogen which has been consumed, until a sample gives a negative peroxide test. The consumption of hydrogen is 32.2 standard liters (96% of theory).

The contents of the hydrogenation reactor, except for a residue of approx. 200 ml, are worked up by being filtered with suction through a frit. The catalyst remaining in the smaller portion of the hydrogenation solution in the hydrogenation reactor is used further for the reductive cleavage according to the invention, without regeneration or working up, by feeding fresh ozonized solution of methyl methacrylate into the reactor via the metering vessel, and the hydrogenation process is repeated under the reaction conditions indicated. A total of 7.5 moles of ozonized methyl methacrylate are cleaved reductively in five such reaction cycles. The total consumption of hydrogen is 159.2 standard liters (94.8% of theory). The combined hydrogenation solutions are worked up by being freed from sodium by stirring with a strongly acid ion exchanger (Lewatit), and the solvent is then removed in vacuo, together with the formaldehyde produced during the reaction as an accompanying product in the form of dimethyl acetal. The residue containing the reaction product is purified by fractionation in vacuo. This gives 698 g of methyl pyruvate boiling at 61°–62° C./40, corresponding to a yield of 91.2% of theory.

EXAMPLE 6 ethyl α-ketobutyrate 192 g (1.5 moles) of ethyl ethylacrylate are dissolved in 1 liter of ethanol and reacted with ozone at $-35°$ to $-30°$ C., and subsequently hydrogenated, analogously to the procedure indicated in Example 5.

The consumption of hydrogen is 32.4 standard liters, corresponding to 96.4% of theory. Working up is carried out as in Example 5, and vacuum rectification gives 171 g of pure ethyl α-ketobutyrate boiling as 68°–69° C./20, corresponding to a yield of 87.7% of theory.

EXAMPLE 7 diethyl mesoxalate 258 g of diethyl methylenemalonate, prepared by a Knoevenagel condensation of malonic ester and formaldehyde, are dissolved in 1 liter of methanol and reacted with ozone, and subsequently hydrogenated, analogously to the procedure indicated in Example 5. 5 g of 10% Pd-on-C in 200 ml of methanol are initially taken as the hydrogenation catalyst. The consumption of hydrogen is 28.9 standard liters (86% of theory). Working up as in Example 5 and rectification in vacuo gives 214 g of diethyl mesoxalate boiling at 110°–112° C./20, corresponding to a yield of 82% of theory.

EXAMPLE 8

3,3-dimethoxypropanal 174 g (1.5 moles) of 4,4-dimethoxybutene are dissolved in 1 liter of methanol and reacted with the equivalent amount of ozone by passing in an ozone/air mixture while being cooled at −110° to 0° C. The absorption of ozone in the reaction mixture is quantitative, and the content of 4,4-dimethoxybutene after the completion of the ozonization is less than 1% of the initial amount.

A suspension of 0.5 g of Pt in 200 ml of methanol is initially placed in a hydrogenation reactor filled with hydrogen, and the ozonization solution is added dropwise at such a rate that the peroxide content in the hydrogenation solution does not exceed 0.05 mole/l at the start and in the course of the entire hydrogenation. Hydrogenation is carried out at 35°–40° C. with vigorous stirring and with continuous replenishment of the hydrogen consumed, while a pH value of 3 to 4, checked by automatic titration with methanolic NaOH solution, is maintained, the hydrogenation solution being completely free from peroxides a few minutes after the completion of the addition of the ozonization solution. The absorption of hydrogen is 31.6 standard liters, corresponding to 94% of theory.

The bulk of the hydrogenation solution is removed with suction from the hydrogenation reactor via a frit, and a peroxide solution which has been prepared by ozonizing 144 g of 4,4-dimethylbutene in methanol is again added, with the maintenance of the peroxide concentration indicated above, to the residual volume of about 200 ml remaining, together with the catalyst, in the reactor, and hydrogenation is carried out.

When the hydrogenation is complete, the entire hydrogenation solution is removed with suction from the reactor via a frit, and the solutions are combined and freed from sodium by treatment with a strongly acid ion exchanger. The methanol is removed in vacuo together with the water of hydrogenation, and the residue is purified by rectification. This gives 314 g of pure 3,3-dimethoxypropanol boiling at 75° C./50, corresponding to a yield of 89% of theory.

EXAMPLE 9

3,3-di-n-butoxypropanal 300 g of 4,4-di-n-butoxybutene are dissolved in 1 liter of methanol and are reacted with ozone, and subsequently hydrogenated, analogously to the procedure indicated in Example 8. The hydrogenation is carried out in such a way that the content of peroxides in the hydrogenation solution does not exceed 0.02 mole/liter, and a pH value between 4 and 5 and a temperature of 35° C. are maintained. The consumption of hydrogen is 32.4 standard liters, corresponding to 96% of theory.

After the catalyst has been removed, the mixture is worked up as in Example 8, 284 g of 3,3-di-n-butoxypropanal boiling at 86° C./50, corresponding to a yield of 93.7% of theory, being obtained.

EXAMPLE 10 succindialdehyde 81 g (0.75 mole) of 1,5-cyclooctadiene are diluted with methanol to a volume of 1 liter. An $O_2/O_3$ mixture containing 4% by weight of ozone is passed into this solution at −10° to −5° C. until 1.5 moles of ozone have been introduced into the solution. In order to prevent losses of volatile constituents, the exit gas is condensed and the condensate is returned to the ozonization. The absorption of ozone is quantitative.

1 g of platinium, prepared in situ by hydrogenating $PtO_2$, is initially taken up in 200 ml of methanol in a hydrogenation reactor, and the suspension is blanketed with hydrogen. The solution obtained in the ozonization is fed continuously into the hydrogenation solution, with vigorous stirring and at a temperature of 30° to 40° C., at such a rate that the peroxide concentration in the hydrogenation reactor does not exceed 0.1 mole/l at the start and in the course of the hydrogenation. The hydrogen consumed during the hydrogenation is replenished continuously, and the consumption is measured. The pH value in the solution is kept at 214 5 by automatic titration with methanolic sodium hydroxide solution. A few minutes after the completion of the addition of the ozonization solution the absorption of hydrogen ceases and the solution becomes completely free from peroxides. 32.6 standard liters of hydrogen are absorbed, corresponding to 97% of theory.

The contents of the hydrogenation reactor, except for a residual volume of about 200 ml, which also contains the catalyst, are removed by suction and the ozonization and reductive cleavage described above are repeated a further 10 times without regenerating or working up the catalyst. A total of 8.25 moles of 1,5-cyclooctadiene are reacted in this way with 16.5 moles of ozone. The total consumption of hydrogen is 355.3 standard liters, corresponding to 96.1% of theory. The total yield of succindialdehyde is determined by oxime titration and is 15.8 moles (96% of theory).

After being freed from catalyst, the combined reaction solutions are freed from sodium by being stirred with a strongly acid iron exchanger and are concentrated under a slight vacuum in a thin film evaporator. For characterization, the residue is acetalized in methanol with acid catalysis, and the reaction mixture thus obtained is fractionated in vacuo. This gives 2,550 g of 1,1,4,4-tetramethoxybutane boiling at 86°–88° C./15, corresponding to a yield of 86.8% of theory, together with trace amounts of 2,5-dimethoxytetrahydrofuran.

EXAMPLE 11 adipaldehyde 123 g of cyclohexene are dissolved in 1 liter of methanol and are reacted with ozone, and subsequently hydrogenated, analogously to the procedure indicated in Example 10. The exit gas from the ozonization is extracted by washing with methanol in order to recover the volatile cyclohexene, and the methanolic wash solution is returned to the ozonization reactor. This measure makes it possible to restrict the loss of cyclohexene to such an extent that, after the end of the ozonization, 94% of the theoretical amount of peroxide, relative to the initial content of cyclohexene, are present in the solution.

The consumption of hydrogen during the hydrogenation is 30.5 standard liters, corresponding to 96.7% of theory, relative to the amount of peroxide recorded above.

After the catalyst has been separated off and the sodium ions have been removed by treating the solution with a strongly acid ion exchanger, a total yield of adipaldehyde of 1.41 moles (94% of theory) is determined by oxime titration. For characterization, the adipaldehyde is acetalized, which gives 275 g of 1,1,6,6-tetramethoxyhexane boiling at 111° C./20, corresponding to a yield of 89% of theory.

EXAMPLE 12

1,8-octanedial 165 g (1.5 moles) of cyclooctene are reacted with the equivalent amount of ozone, and subsequently hydrogenated, as in Example 10. The absorption of hydrogen is 32.2 standard liters, corresponding to 95.8% of theory. When the catalyst has been removed, oxime titration indicates a content of 1.42 moles of 1,8-octanedial (94% of theory). The reaction product is characterized and isolated by adjusting the pH of a solution of the 1,8-octanedial in methanol to a value of 1 by treatment with mineral acids, and allowing this solution to stand for some hours in order to form the acetal.

When the formation of the acetal is complete, the solution is neutralized under cold conditions and diluted with water. In the course of this, 1,1,8,8-tetramethoxyoctane separates out as a water-insoluble oil; it is separated off and the remaining solution is extracted with petroleum ether. The product phases are combined, freed from petroleum ether and fractionated in vacuo. This gives 322 g of 1,1,8,8-tetramethoxyoctane boiling at 147°–149° C./30, corresponding to 91.7% of theory.

EXAMPLE 13

3-thiaglutaraldehyde 3,3-dioxide 177 g of sulfolene are reacted with ozone, and subsequently hydrogenated, as in Example 10. The absorption of $H_2$ is 32.3 standard liters, corresponding to 96.1% of theory.

After the removal of the catalyst, oxime titration indicates a content of 2.87 moles of aldehyde groups (95.8% of theory).

The solvent is removed in vacuo on a rotary evaporator, giving 219 g of a pale yellow residue. The content of aldehyde groups per gram corresponds to 13.0 m moles, corresponding to a total yield of 3-thiaglutaraldehyde 3,3-dioxide of 94.9% of theory.

EXAMPLE 14 homophthalaldehyde 87 g of indene (0.75 mole) are dissolved in 0.5 liter of methanol and ozonized and hydrogenated analogously to the procedure indicated in Example 10. The absorption of $H_2$ is 16.1 standard liters. After the removal of the catalyst, determination of aldehyde groups of oxime titration indicates a content of 41.1 moles (94% of theory).

Part of the solution is concentrated on a rotary evaporator, and the resulting homophthalaldehyde is characterized as the di-p-nitrophenylhydrazone, melting point 217°–218° C.

EXAMPLE 15 dimethyl 1,6-hexanedial-3,4-dicarboxylate 297 g (1.5 moles) of dimethyl tetrahydrophthalate are dissolved in 1 liter of methanol and are ozonized and hydrogenated as in Example 10. The absorption of $H_2$ is 31.4 standard liters. After the hydrogenation and the removal of the catalyst, a completely peroxide-free solution is obtained, in which determination of aldehyde groups by oxime titration indicates a content of 2.86 moles (95.3% of theory). The solution is freed from sodium by treatment with a strongly acid ion exchanger, water is added to the solution of the product, and methanol is distilled off. The ester is thus saponified, and 650 g of an aqueous solution of 1,6-hexanedial-3,4-dicarboxylic acid are obtained; this has an aldehyde group content of 2.83 moles and a carboxylic acid group content of 2.94 moles (94.3% and 98%, respectively, of theory, calculated in each case on 1,6-hexanedial3,4-dicarboxylic acid).

EXAMPLE 16 o-phthalaldehyde 96 g (0.75 mole) of naphthalene are dissolved as far as possible in 1 liter of methanol and are reacted with the equivalent amount of ozone, and subsequently hydrogenated, analogously to the instructions in Example 10. Care is taken to ensure good mixing during the ozonization, so that as yet undissolved naphthalene dissolves to take the place of the naphthalene which has reacted.

After the completion of the ozonization less than 2.5% of the original amount of naphthalene are present in the solution. The absorption of hydrogen during the hydrogenation is 31.6 standard liters, corresponding to 94% of theory.

The mixture is worked up by filtering off the catalyst, distilling off the methanol and taking up the residue in sufficient hot water to give a clear solution. On standing under cold conditions, part of the o-phthalaldehyde crystallizes out and is separated off. The aqueous phase is extracted twice with diethyl ether, the product which has crystallized out and been separated off previously is dissolved in the combined ether phases, and the organic solvent is evaporated off. This gives 87 g (86.5% of theory) of o-phthalaldehyde in the form of a yellow solid in which determination of aldehyde groups indicates a content of 14.8 m moles/g (99% of the theoretical content of aldehyde groups) and which has an uncorrected melting point of 54° C.

EXAMPLE 17

3-oxaglutaraldehyde 105 g of 2,5-dihydrofuran are reacted with ozone at −20° C., and subsequently hydrogenated, as in Example 10. The exit gas from the ozonization is extracted by washing with methanol in order to recover the volatile 2,5-dihydrofuran, and the methanolic wash solution is returned to the ozonization reactor. This measure makes it possible to restrict the loss of 2,5-dihydrofuran to such an extent that, after the end of the ozonization, 95.3% of the theoretical amount of peroxide, relative to the initial content of 2,5-dihydrofuran, are present in the solution.

The consumption of hydrogen during the hydrogenation is 31.9 standard liters, corresponding to 94.9% of theory. In the solution of the product, oxime titration indicates an aldehyde group content of 2.88 moles, corresponding to a yield of 3-oxaglutaraldehyde of 96% of theory.

What I claim is:

1. Process for preparing monocarbonyl or biscarbonyl compounds of the formula

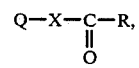

$$Q-X-\underset{\underset{O}{\|}}{C}-R, \qquad I$$

wherein Q represents hydrogen or the radicals

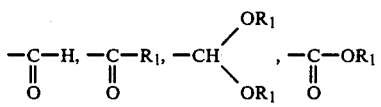

in which

R$_1$ is C$_1$ to C$_6$ alkyl;

X represents linear or branched alkylene having 1 to 20 C atoms, linear or branched alkylene having 2 to 20 C atoms in which one —CH$_2$-group of the alkylene chain is replaced by oxygen or the —SO$_2$-group, substituted linear or branched alkylene having 1 to 20 C atoms, this alkylene being substituted by one or more groups which are inert under the reaction conditions; aralkylene or alkylenearylene having 7–12 C atoms each; substituted aralkylene or alkylenearylene having 7–12 C atoms each, the substituent being a group which is inert under the reaction conditions; o-, m-, or p-phenylene, substituted o-, m- or p-phenylene, the substituent being a group which is inert under the reaction conditions; a divalent five-membered or six-membered heterocyclic radical, containing one or two heteroatoms in the heterocyclic ring; or a single bond between two adjacent C-atoms; and R represents hydrogen, C$_1$ to C$_4$ alkyl or the group

wherein R$_1$ is defined as above; glyoxal, alkylglyoxals and dialkylacetals thereof being disclaimed from the formula I, said process consisting of (a) reacting an unsaturated compound of the formula

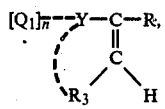    II wherein n is 0 or 1, Q$_1$ represents hydrogen or the radicals

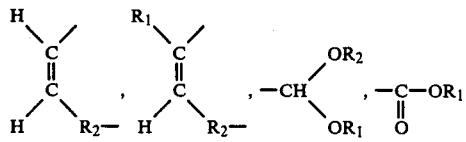

in which

R$_1$ is C$_1$ to C$_6$ alkyl;

R$_2$ and R$_3$ independently of one another represent hydrogen C$_1$ to C$_4$ alkyl or, if n is 1 and Q$_1$ represents the radical

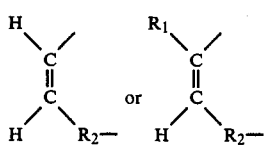

R$_2$ and R$_3$ together can be a further single bond between two adjacent C atoms or alkylene having 2 to 4 carbon atoms; Y has the same meaning as X in formula I if n is 1, or, if n is o, Y together with R$_3$ represents linear or branched alkylene having 2 to 20 C atoms, linear or branched alkylene having 2 to 20 C atoms in which one —CH$_2$-group of the alkylene chain is replaced by oxygen or the —SO$_2$-group, substituted linear or branched alkylene having 2 to 20 C atoms, this alkylene being substituted by one or more groups which are inert under the reaction conditions, aralkylene or alkylenearylene having 7–12 C atoms, substituted aralkylene or alkylenearylene having 7–12 C atoms, the substituent being a group which is inert under the reaction conditions; and R is defined as in formula I, is reacted in a lower aliphatic alcohol, at temperatures from −80° C. to +20° C. with the equivalent amount of ozone to yield a peroxide-containing solution of the ozonisation products of the compound of formula II (b) hydrogenating the peroxide-containing solution of the ozonisation products thus obtained at pH 2 to 7 and at temperatures from 15° to 45° C., said solution being fed continuously, while hydrogen is passed in under a pressure of 1 to 20 bar, into a suspension of a noble metal catalyst in the lower aliphatic alcohol used in stage (a), at such a rate that, over the entire course of hydrogenation, a peroxide content of not more than 0.1 mole/l is set up and maintained in the suspension, whereby the ozonisation products are cleaved reductively into the corresponding carbonyl compound, and then separating the carbonyl compound so formed.

2. The process according to claim 1, in which the compound of formula II is reacted with ozone in stage (a) at temperatures within the range from −15° to 0° C.

3. The process according to claim 1, in which methanol is used as the solvent in stage (a) and in stage (b).

4. The process according to claim 1, in which a peroxide content of not more than 0.02 mole/l is set up or maintained in the suspension for the hydrogenation of the ozonization products in stage (b).

5. The process according to claim 1, in which platinum without a supporting material is used as the catalyst for the hydrogenation in stage (b).

6. The process according to claim 1, in which the hydrogenation in stage (b) is carried out within the temperature range from 30° to 40° C.

7. The process according to claim 1, in which the pH is adjusted to a value of 3 to 5 during the hydrogenation in stage (b).

8. The process according to claim 1 in which the unsaturated compound used as starting material has the formula

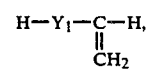    IIa wherein Y$_1$ together with hydrogen represents a phenyl substituted in the ortho-, meta-, or para-position by a substituent which is inert under the reaction conditions or represents a six-membered heterocyclic radical having one heteroatom in the ring.

9. The process according to claim 8 in which the unsaturated compound used as starting material has the formula IIa, wherein $Y_1$ together with hydrogen is p-nitrophenyl, p-tolyl, 2-pyridinyl or 4-pyridinyl.

10. The process according to claim 1, in which the unsaturated compound used as starting material has the formula

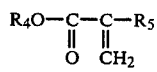   IIb wherein $R_4$ is methyl or ethyl and $R_5$ is methyl, ethyl or the ethoxycarbonyl radical.

11. The process according to claim 10, in which the compound of formula IIb is methyl methacrylate.

12. The process according to claim 1, in which the unsaturated compound used as starting material has the formula

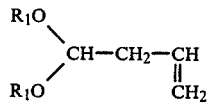   IIc wherein $R_1$ is as defined in formula I.

13. The process according to claim 1, in which the unsaturated compound used as starting material has the formula

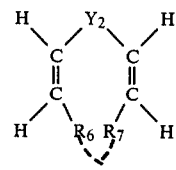   IId wherein $Y_2$ is o-phenylene or alkylene having 2 to 4 C atoms and $R_6$ and $R_7$ together represent a single bond between two adjacent C atoms or alkylene having 2 to 4 C atoms.

14. The process according to claim 1, in which the unsaturated compound used as starting material has the formula

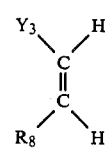   IIe wherein $Y_3$ and $R_8$ together are selected from the group consisting of alkylene having 2 to 6 C atoms, $-CH_2-SO_2-CH_2-$, $-CH_2-O-CH_2-$,

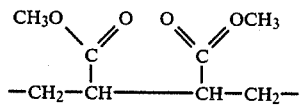 and 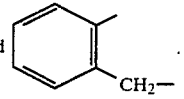

* * * * *